US010653605B2

(12) United States Patent
Moya Argilagos et al.

(10) Patent No.: US 10,653,605 B2
(45) Date of Patent: May 19, 2020

(54) DENTIFRICE COMPOSITION

(75) Inventors: Dally Moya Argilagos, Zurich (CH); Cornelia Scheffel, Aesch (CH); Turan Matur, Bottmingen (CH); Andre Brunella, Dornach (CH)

(73) Assignee: GABA International Holding GmbH, Therwil (CH)

( * ) Notice: Subject to any disclaimer, the term of this patent is extended or adjusted under 35 U.S.C. 154(b) by 409 days.

(21) Appl. No.: 13/985,570

(22) PCT Filed: Feb. 18, 2011

(86) PCT No.: PCT/EP2011/052473
§ 371 (c)(1),
(2), (4) Date: Aug. 14, 2013

(87) PCT Pub. No.: WO2012/110106
PCT Pub. Date: Aug. 23, 2012

(65) Prior Publication Data
US 2013/0323186 A1 Dec. 5, 2013

(51) Int. Cl.
A61K 8/21 (2006.01)
A61K 8/73 (2006.01)
A61Q 11/00 (2006.01)

(52) U.S. Cl.
CPC ............... *A61K 8/736* (2013.01); *A61K 8/21* (2013.01); *A61Q 11/00* (2013.01); *A61K 2800/88* (2013.01)

(58) Field of Classification Search
CPC . A61K 8/21; A61K 8/41; A61K 8/736; A61K 2800/88; A61Q 11/00
See application file for complete search history.

(56) References Cited

U.S. PATENT DOCUMENTS

| | | | |
|---|---|---|---|
| 2,839,448 A | 6/1958 | Hager et al. | |
| 5,188,820 A | 2/1993 | Cummins et al. | |
| 6,350,436 B1* | 2/2002 | Glandorf et al. | 424/52 |
| 6,372,198 B1 | 4/2002 | Abbate | |
| 6,521,216 B1 | 2/2003 | Glandorf et al. | |
| 6,638,918 B2 | 10/2003 | Davidson et al. | |
| 8,980,229 B2 | 3/2015 | Pilch et al. | |
| 2004/0013690 A1 | 1/2004 | Portnoy et al. | |
| 2007/0025928 A1* | 2/2007 | Glandorf | A61K 8/20 424/49 |
| 2007/0116652 A1* | 5/2007 | Kamath et al. | 424/58 |
| 2009/0136432 A1* | 5/2009 | Strand et al. | 424/52 |

FOREIGN PATENT DOCUMENTS

| | | |
|---|---|---|
| CN | 1969801 | 5/2007 |
| GB | 2132889 | 7/1994 |
| JP | S56-045408 | 4/1981 |
| JP | H05-000930 | 1/1993 |
| JP | H06-084309 | 10/1994 |
| JP | H08-026952 | 1/1996 |
| JP | H09-249541 | 9/1997 |
| JP | 2006-241122 A | 9/2006 |
| WO | 2000/032160 | 6/2000 |
| WO | WO 01/058146 | 8/2001 |
| WO | WO 02/017868 | 3/2002 |
| WO | WO 03/042251 | 5/2003 |
| WO | WO 04011011 | 2/2004 |
| WO | WO 04/045446 | 6/2004 |
| WO | WO 06/005211 | 1/2006 |
| WO | WO 06052476 | 5/2006 |
| WO | WO 08/121518 | 10/2008 |
| WO | WO 2009/099450 | 8/2009 |
| WO | WO 2009/130319 | 10/2009 |
| WO | WO 2010/019587 | 2/2010 |
| WO | WO 12/087327 | 6/2012 |

OTHER PUBLICATIONS

Dentifrices and mouthwashes ingredients and their use. Dec. 31, 2003, p. 6, 2nd paragyaph; pp. 16 and 19. Retrieved from https://www.duo.uio.no/bitstream/handle/10852/33076/Storehagen_Ose_Midha.pdf.
Schlueter N. et al., "Tin-containing fluoride solutions as anti-erosive agents in enamel: an in vitro tin-uptake, tissue loss, and scanning electron micrograph study", European Journal of Oral Sciences, 2009, vol. 117, pp. 427-434.
Wiilknitz P., Cleaning Power And Abrasivity Of European Toothpastes. Adv Dent Res., Nov. 30, 1997, vol. 11, No. 4, pp. 576-579, Abstract.
Arnaud et al., 2010, "Chitosan Effect on Dental Enamel De-Remineralization: An in vivo Evaluation," J. Dentistry 38(11):848-852.
Chitodent, 2004, "Chitodent—the Homeopathically Compliant, Fluoride-Free Toothpaste with Chitosan," Product Information from website www.chitodent.de.
Database GNPD MINTEL, 2010, "Moutwash," AN: 1405361.
Ganss et al., 2010. "Erosionen der Zahnhartsubstanzen—Pravention und Therapie," Quintessenz 61:1203-1210—Awaiting translation due Aug. 13, 2013—Ref. No. 42133.
Hjortsjo et al., 2009, "Effect of Stannous Fluoride and Dilute Hydrofluoric Acid on Early Enamel Erosion over Time in vivo," Caries Research 43(6):449-454.
International Search Report and Written Opinion in International Application No. PCT/EP2011/052473, dated Feb. 7, 2012.

(Continued)

Primary Examiner — Lezah Roberts

(57) ABSTRACT

A dentifrice, such as toothpaste, containing chitosan or pharmaceutically acceptable acid addition salt thereof with fluoride ions, for use against erosive tooth demineralization, and kits containing chitosan or pharmaceutically acceptable acid addition salt thereof with fluoride ions, wherein one of the two active agents is comprised in a dentifrice, are described. The dentifrice in the form of toothpaste may furthermore comprise dissolved tin, in particular stannous ions. Toothpastes containing chitosan or pharmaceutically acceptable acid addition salt thereof with fluoride ions are tested in the treatment or prevention of erosive tooth demineralisation caused by citric acid.

9 Claims, No Drawings

(56) References Cited

OTHER PUBLICATIONS

Schlueter et al., 2009, "Efficacy of an Experimental Tin-F-Containing Solution in Erosive Tissue Loss in Enamel and Dentine in situ," Caries Research 43(6):415-421.
Willumsen et al., 2004, "Effects from Pretreatment of Stannous Fluoride Versus Sodium Fluoride on Enamel Exposed to 0.1 M or 0.01 M Hydrochloric Acid," Acta Odontol. Scand. 62:278-281.
Written Opinion in International Application No. PCT/EP2011/052473, dated Feb. 19, 2013.
Young et al., 2006, "Effect of Stannous Fluoride Toothpaste on Erosion-Like Lesions: an in vivo Study," Eur. J. Oral Sci. 114(3):180-183.
Schemehorn et al., 2011, "Abrasion, polishing, and stain removal characteristics of various commercial dentifrices in vitro," J. Clinical Dentistry 22(1):11-18.
Arnaud, 2008, "Characterization and Application of Chitosan in the Processes of Des-Remineralization of Dental Enamel," Dissertação de Mestrado, Universidade Federal de Pernambuco, Centro de Ciências Exatas e da Natureza, Master's Thesis in Brazil (Abstract on pp. 11-12 in English).

\* cited by examiner

DENTIFRICE COMPOSITION

FIELD OF THE INVENTION

The present invention relates to the use of dentifrices in treating or preventing erosive tooth demineralization in acidic media, brought about by food acids or endogenous acids such as gastric juice.

BACKGROUND OF THE INVENTION

There are three major sources for acids, which can cause tooth demineralization. The first source are the acids generated by cariogenic oral bacteria from food debris. These acids are carboxylic acids derived from the carbohydrates of the food debris that are metabolized by the oral bacteria. Such acids are rather weak, but act for extended periods on the teeth. The second source is the exogenous food acids that are present in the foodstuffs themselves, in particular in fruits, fruit juices or in artificial soft drinks, or in salad dressings. The third source are endogenous acids, in particular hydrochloric acid-containing gastric juice, which may come into contact with the teeth upon vomiting, such as in bulimia patients, or in reflux disease patients. These latter two types of acids are rather strong but act only for short times on the teeth. Tooth demineralisation caused by the latter two types of acids is termed "erosive tooth demineralisation" and is not related to cariogenic oral bacteria. Since acid-containing soft drinks have enjoyed a rising popularity among consumers in the past time the problem of erosive tooth demineralisation by food acids has become more acute, and a marked percentage of the overall population is nowadays afflicted by it. Similarly, a rising number of (mainly female) patients are subject to bulimia. Erosive tooth demineralisation is not noticed by the afflicted subject for quite a long time, and the pathological condition is thus often only diagnosed at a very late stage. Since erosive tooth demineralisation is considered irreversible (in contrast to tooth demineralization caused by cariogenic bacteria) it is essential that it be prevented from happening in the first place, or if it has already taken place, that it be prevented from proceeding further or that its progression be slowed down.

Fluorides are customarily used in oral care products such as toothpastes, dental gels or mouthrinses. It has been known for a long time that fluoride ion, optionally in combination with stannous ions, such as in the form of stannous fluoride, is beneficial in preventing erosive tooth demineralisation.

Chitosan has occasionally been used or studied in oral care. GB 2132889A describes oral care products containing chitin derivatives such as chitosan, and discloses that chitin or chitosan may act as a cure or prophylaxis in case of dental caries, periodontoclasia and halitosis, and that in a dentifrice chitosan salts may mask the taste of a silica abrasive. WO 02/17868A describes oral and dental hygiene agents containing chitosan microcapsules, the microcapsules being loaded with an active agent which may be, among others, stannous fluoride. Its compositions are said to have protective effect against caries, periodontosis and plaque, and to have anti-inflammatory effect. WO 03/042251A discloses compositions, such as oral care compositions, comprising chitosan in the form of nano-sized fibres and which also may contain a fluoride source. These compositions are said to improve general gum and teeth health, to be suitable for treatment of halitosis and gingivitis, to reduce staining of the teeth, to provide anti-caries, anti-plaque and anti-calculus benefits, to inhibit cariogenic bacteria, and to inhibit hydrogen sulphide and volatile odiferous organosulphide compounds produced by salivary microorganisms. For the chitosan itself it is stated that it has film-forming and pH-buffering capabilities. JP 2006/241122A discloses compositions, which may be oral care compositions, which comprise glucosamine and/or chitosan oligosaccharide, and a remineralisation promotion constituent containing a fluorine ion source. The "remineralisation" is in the case of carious lesions produced by *streptococcus mutans*. WO 2008/121518A discloses polymeric microcapsules, which may preferably be chitosan microcapsules, and which may be used in dentifrices which may contain a fluoride source. The capsules also contain a quaternary ammonium salt. The compositions are said to be antimicrobial. Recently a toothpaste called "Chitodent" has appeared on the German market. According to its advertisement it contains chitin, chitosan and silver ions, but is devoid of fluoride. Stamford Arnaud T M et al. J Dent 38 (2010)848-852 studied the remineralising effect of chitosan in human tooth samples which had been demineralized with acetate buffers of pH 4.0 and 4.8, which is a model for caries-related demineralization. Ganss C, Schlüter S. Quintessenz 61 (2010)1203-1210 discusses prospective new agents for the indication of erosive tooth demineralisation and mentions chitosan but states that "proof of activity so far is not available". In a poster by Neutard et al. presented at the 57th congress of the European Organization for Caries Research (ORCA, Montpellier, France, July 2010), activities of some fluoride-containing toothpastes and some "special free fluoride-free toothpastes" (among which was the above mentioned Chitodent) in the prevention of erosive tooth demineralisation were determined. The authors concluded that "the fluoride-free preparations had no significant effect" and that "the special formulations were not superior or even less effective compared to conventional products".

The present application seeks to provide new treatment and prevention routes against erosive tooth demineralisation caused by strong food acids or strong endogenous acids such as gastric juice.

BRIEF SUMMARY OF THE INVENTION

The task set is solved by a dentifrice comprising chitosan or a pharmaceutically acceptable acid addition salt thereof; fluoride ions and an abrasive, for use against erosive tooth demineralization.

Further objects of the invention are:

A kit comprising:
a) A dentifrice comprising a combination of chitosan or pharmaceutically acceptable acid addition salt thereof, fluoride ions and an abrasive; and
b1) a container containing the dentifrice and bearing human-readable indications disclosing that the dentifrice is for use against erosive tooth demineralization, or
b2) a package containing a container, the container comprising the dentifrice, and the package bearing human-readable indications disclosing that the dentifrice is for use against erosive tooth demineralization, or
b3) a package containing a container and a leaflet, the container comprising the dentifrice, and the leaflet bearing human-readable indications disclosing that the dentifrice is for use against erosive tooth demineralization.

A method for the prevention of erosive tooth demineralisation or for the treatment of teeth affected by erosive tooth demineralisation in a subject in need of such prevention or treatment, comprising bringing the subject's teeth in contact with a dentifrice comprising chitosan or a pharmaceutically acceptable acid addition salt thereof, fluoride ions and an abrasive.

Oral care articles containing fluoride ions as an agent against erosive tooth demineralization, and chitosan or a pharmaceutically acceptable acid addition salt thereof, as a combination for the simultaneous, separate or successive administration in the prevention or treatment of erosive tooth demineralisation, with the provisos that the oral care articles contain a dentifrice comprising an abrasive, and that either the fluoride ions or the chitosan or pharmaceutically acceptable acid addition salt thereof are contained in the dentifrice.

A toothpaste comprising a liquid phase, 200 to 2000 ppm, preferably 1000 to 1800 ppm fluoride ions, 0.05 to 1% of chitosan or a pharmaceutically acceptable acid addition salt thereof, 3000 to 4000 ppm tin dissolved in the liquid phase, 17 to 27% of glycerol, 17 to 27% of sorbitol and 0.3 to 1% of gluconate, all % being based on the toothpaste; and one or more abrasives in a total amount such as to impart the toothpaste a PCR value of at least 50.

Preferred embodiments of all these objects are as in the respective dependent claims and as outline hereinafter.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The invention requires, as a first essential component, chitosan or a pharmaceutically acceptable acid addition salt thereof. The chitosan may be derived from chitin originating e.g. from the shells of marine crustaceans (e.g. crab, shrimp, prawn, krill, lobster, crayfish, barnacle, copepod), from insects or from fungi. The chitosan may preferably have a degree of deacetylation (DDA) of 50% to 99%, more preferably of 70% to 95% and even more preferably of 75% to 90%. The DDA (in percent) of a chitosan sample may be obtained by titration as described in example 13. The chitosan is preferably in a form where its deacetylated amino groups are protonated with a pharmaceutically acceptable acid, to form a pharmaceutically acceptable acid addition salt of the chitosan. The protonation degree, i.e. the mole fraction of deacetylated amino groups that are protonated, is preferably in the range of 80 mole % to 99 mole %, more preferably in the range of 90 mole % to 95 mole %. As pharmaceutically acceptable acids that can be used to form the pharmaceutically acceptable acid addition salt thereof may be mentioned mineral hydrohalic acids, such as hydrochloric or hydrofluoric acids; mineral oxo acids, such as sulfuric, phosphoric, or nitric acids; or organic carboxylic acids. The chitosan or pharmaceutically acceptable acid addition salt thereof preferably has an average molecular weight in the range of 5 000 to 1 000 000 Daltons, more preferably in the range of 5 000 to 500 000 Daltons, particularly preferably in the range of 100 000 to 400 000 Daltons. This average molecular weight and molecular weight distribution may be determined in a known manner by gel permeation chromatography using e.g. N-acetyl-D-glucosamine oligomer and pullulan retention time standards, or by using a multi angle laser light scattering (MALLS) detector.

Preferably, the chitosan is not further chemically modified by additional functional groups such as hydrophilic or charged side groups, N-carboxymethyl, N,N-dicarboxymethyl, N-methylene phosphonic, N-methyl, N-monocarboxybutyl, N,N-dicarboxybutyl, 5-methylpyrrolidinone and N-trimethyl This is referred as an unmodified chitosan.

The invention requires, as a second essential component, fluoride ions. The fluoride ions may be used in the form of any fluoride ion source customarily employed in oral care compositions, such as stannous fluoride, sodium fluoride, amine fluoride or hydrofluoric acid.

The two essential components are used according to the invention in such a form that at least one of the two is contained in a dentifrice containing an abrasive. As "dentifrice containing an abrasive" are understood in particular toothpastes and dental powders; by such term dental gels are excluded, the latter being devoid of abrasives. When the dentifrice is a toothpaste, it preferably has one or more abrasives of a type and in a total amount such that the overall toothpaste has a PCR value of at least 50, preferably at least 60, more preferably 60 to 90. This allows to achieve a satisfactory cleaning performance. By the co-use of the fluoride ions and of the chitosan or pharmaceutically acceptable acid addition salt thereof, whether contained in one and the same toothpaste containing an abrasive, or split up in a toothpaste containing an abrasive and another formulation, to be used in combination (see below), it is surprisingly possible to achieve a high PCR while still be usable on teeth affected by erosive tooth demineralisation and protecting from erosive tooth demineralization. For the purposes of the invention any PCR values are determined as described in example 14. The abrasives that can be used themselves are conventional. Preferred abrasives are inorganic abrasives, such as precipitated silicas, aluminas, insoluble carbonates (e.g. calcium carbonate, calcium phosphate, calcium pyrophosphate), zeolites or stannous pyrophosphate; or organic abrasives such as polyethylene, polyvinyl chloride, polystyrene, polycarbonate, copolymers from (meth)acrylates and other olefinic monomers, polyamides, urea-formaldehyde resins, melamine-formaldehyde resins, phenol-formaldehyde resins, cured, pulverised epoxy resins or polyesters. A mixture of these abrasives may also be used. The skilled person in the art is well aware on how to choose the type(s) and amount(s) of abrasive(s) to achieve the preferably intended PCR values. Preferred is an abrasive mixture of hydrated silica(s) with a small amount, such as 5 to 20% based on the total of the hydrated silica(s), of alumina. Toothpastes suitable for the uses of the invention may also comprise essentially non-abrasive silicas, having only a thickening effect on the toothpaste formulations.

The main distinction between a toothpaste and a dental powder is that the former also comprises a liquid phase, whereas the latter is a dry powder which is slurried in the oral cavity upon use with saliva. The use according to the invention in the form of a toothpaste is preferred. In the latter case it is preferred that anyone of the two essential components that is contained in the toothpaste be dissolved in its liquid phase.

The dentifrices, articles or kits of the invention are for use against, and are efficacious in, the treatment or prevention, particularly the prevention of erosive tooth demineralisation caused by food acids (i.e. acids originating from foods) or by endogenous acids such as gastric juice (hydrochloric acid).

As "food acids" are considered in the context of the present application such acids with a pKa value (or first pKa value, if multibasic) of 5.0 or less. Examples therefor are citric acids (e.g. from fruits), tartaric acid (e.g. from wine), oxalic acid (e.g. from rhubarb), phosphoric acid (e.g. from soft drinks), hydrated sulphur dioxide (e.g. from wine), and amino acids.

The chitosan or a pharmaceutically acceptable acid addition salt thereof and the fluoride ions may either be contained in a single dentifrice, containing them as a "fixed" combination. They may on the other hand be included into separate oral care formulations, wherein one formulation contains the chitosan and/or pharmaceutically acceptable salt thereof and the other oral care formulation contains the fluoride, provided that at least one of the two agents is included into a dentifrice containing an abrasive. Such oral care formulation kits, also designated in the following as "oral care articles" or, for short, "articles", may be intended for either simultaneous administration, i.e. the two formulations are used by one and the same subject at the same time, or for separate administration, i.e. the two formulations are used independently by one and the same subject, but not according to a specified dosage regime, or for successive administration, i.e. the two formulations are used by one and the same subject one after the other, in particular one immediately after the other, in particular according to a specified dosage regime.

An example for such an article is a kit containing, as a first oral care formulation, a toothpaste comprising an abrasive and comprising a liquid, in particular aqueous phase, wherein in that liquid phase chitosan or a pharmaceutically acceptable acid addition salt thereof is dissolved; and containing, as a second formulation, a mouthrinse consisting of a liquid, preferably aqueous phase and comprising dissolved fluoride ions. In this exemplary kit, it may also be possible to include the fluoride into the toothpaste, by dissolving in its liquid phase, and the chitosan or pharmaceutically acid addition salt thereof into the mouthrinse. In either of these two variants, optionally and preferably dissolved tin as described hereinbefore may be present, the tin also being preferably dissolved in the mouthrinse or the liquid phase of the toothpaste.

Said articles are preferably intended for separate or sequential use of its two formulations, according to a dosage regime similar to conventional such toothpaste/mouthrinse articles.

The content of dissolved chitosan and/or its pharmaceutically acceptable acid addition salt in the dentifrice (when it is a dentifrice containing both active agents as a "fixed" combination) or in the oral care formulation containing the chitosan or salt thereof (in the case of articles having two or more oral care formulations) is firstly chosen at least sufficiently high such as to observe a statistically significantly higher activity, in combination with the fluoride ions, than is observed in the same experimental setup, but with fluoride ions alone. As "statistically significant" is understood if a two-sided Student's T-test, with a confidence limit of 5%, detects such significant difference in activity between the combination fluoride ions plus chitosan or salt thereof, and fluoride ions alone. Such statistically significant difference is indicative of a synergistic action between fluoride ions and the chitosan or salt thereof. The content of dissolved chitosan and/or its pharmaceutically acceptable acid addition salt is secondly chosen not higher than as to impart the toothpaste (or the liquid phase of the oral care formulation containing the chitosan or salt thereof, in the case of articles having two or more oral care formulations) an overall dynamic viscosity of at the most 1500 Pa*s. The skilled person is well aware on how to choose the proper amount, molecular weight and DDA of the chitosan or pharmaceutically acceptable acid addition salt thereof, in order to achieve, depending on the pH, the ionic strenght and any other viscosity-affecting components of the toothpaste, the desired dynamic viscosity thereof. Typically the amount of chitosan or pharmaceutically acceptable acid addition salt thereof is preferably 0.01 to 5%, more preferably 0.05 to 1%, still more preferably 0.1 to 0.7%, based on the dentifrice, toothpaste or formulation of the article in question.

The fluoride ion content of the dentifrice (when it is a dentifrice containing both active agents as a "fixed" combination) or in the oral care formulation containing fluoride (in the case of articles having two or more oral care formulations) is preferably from 200 to 2000 ppm, based on the dentifrice, or based on the formulation in question. If in a dentifrice/mouthrinse kit the dentifrice is a toothpaste and the fluoride ions are comprised in that toothpaste, then the fluoride ion concentration is more preferably from 1000 to 1600 ppm, most preferably from 1300 to 1500 ppm, based on the toothpaste, wherein the fluoride ions are preferably dissolved in the liquid phase of the toothpaste. The fluoride ion content may be determined potentiometrically using a fluoride-selective electrode (see example 9).

The fluoride ions and the chitosan or pharmaceutically acceptable acid addition salt thereof are preferably dissolved in a liquid phase of a toothpaste. The liquid phase is preferably at least partially aqueous. Accordingly, the liquid phase may preferably comprise about 10% to about 90%, more preferably about 25% to about 75%, based on the liquid phase, of water. The liquid phase may have a pH which is physiologically acceptable and which preferably serves to fully dissolve the entire amount of chitosan. Such pH may typically be in the range of about 3.0 to about 6.0, preferably about 4.0 to about 5.0, more preferably about 4.3 to about 4.6. If necessary the pH of the liquid phase may be adjusted to the desired value by adding acid (such as hydrochloric acid) or base (such as sodium hydroxide).

The toothpastes and any other oral care formulations within articles are preferably devoid of silver, meaning that they comprise preferably less than 0.05%, more preferably less than 0.001%, based on the composition, of silver.

When any dentifrice is a toothpaste having a liquid phase (whether containing both fluoride ions and chitosan or pharmaceutically acceptable salt thereof as a "fixed" combination, or containing only one of these two and forming part of an articles having two or more oral care formulations) then it furthermore preferably also comprises tin dissolved in that liquid phase. The term "dissolved tin", as used herein, is intended to encompass all ionic or non-ionic tin species in the formal oxidation states +II and/or +IV and being dissolved in the liquid phase. Examples of such dissolved tin species are hydrated stannous ions, stannous hydroxide, soluble ionic or nonionic complexes of stannous and/or stannic ions with ligands, such as with an optionally also present dissolved $C_{(3-6)}$ sugar alcohol and/or the anionic conjugate base of an optionally also present dissolved organic acid as ligands, and ionic hydroxo complexes of stannous and/or stannic ions. Preferably 60 mol % or more, more preferably 75 mol % or more of the content of dissolved tin [Sn] is tin in the formal oxidation state +II. For a toothpaste contained within an article it is preferably 3000 to 4000 ppm, more preferably 3300 to 3700 ppm. The total content of dissolved tin may be determined using X-ray fluorescence (see example 7). The content of dissolved tin in the formal oxidation state +II may be determined potentiometrically (see example 8). The dissolved tin may preferably be derived from a pharmaceutically acceptable stannous ion salt. Examples are stannous chloride, stannous fluoride, stannous hydroxide, stannous sulphate, with stannous chloride being preferred.

In the dentifrices and articles intended for the uses and processes of the instant invention, the fluoride ions may be used as any fluoride salt customarily used in the field of oral care, such as stannous fluoride, sodium fluoride, sodium monofluorophosphate and amine fluoride. Preferably the fluoride is used as sodium fluoride and/or as amine fluoride, more preferably as a mixture of sodium fluoride and amine fluoride such that the amount ratio fluoride ions derived from sodium fluoride: fluoride ions derived from amine fluoride is in the range of 0.7:1 to 1.4:1, more preferably 0.9:1 to 1.1:1.

In all embodiments where amine fluoride is used the amine fluoride preferably contains ammonium cations of the formula R—NH$^+$R$_a$—[(CH$_2$)$_u$—NH$^+$R$_b$]$_v$—R$_c$, wherein R is a saturated or unsaturated straight-chain hydrocarbon residue of 10 to 20 carbon atoms, v is an integer from 0 to 1, u is an integer from 2 to 3 and R$_a$, R$_b$ and R$_c$, are independently selected from hydrogen and —CH$_2$CH$_2$OH. The residue R can have even or odd-numbered chain length, residues R having an even-numbered chain length are preferred with regard to physiological acceptability. The residues may be preferably mono-unsaturated. Examples of saturated hydrocarbon residues having an even-numbered chain length are decyl, dodecyl (lauryl), tetradecyl (myristyl), hexadecyl (cetyl, palmityl), octadecyl (stearyl) and eicosanyl. Examples of unsaturated residues having an even-numbered chain length are 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (linolenyl) or 9-cis-eicosaen-1-yl (gadolyl). More preferred are C$_{118}$ alkyl or C$_{118}$ alkenyl, in particular 9-cis-octadecen-1-yl(oleyl). The most preferred cation in all embodiments of the invention is with R=oleyl, R$_a$=R$_b$=R$_c$=—CH$_2$CH$_2$OH, v=1 and u=3, i.e. wherein the amine fluoride is olaflur (N-(9-cis-octadecen-1-yl)-N,N'N'-tris(hydroxyethyl)-1,3-diaminopropane dihydrofluoride). The amount of ammonium cations may be determined according to example 10 or 11.

The toothpastes of the invention may furthermore comprise one or more C$_{(3-6)}$ sugar alcohols. The term "C$_{(3-6)}$ sugar alcohol" is intended to encompass all polyhydric alcohols with a total carbon atom number n of 3 to 6 and a molecular formula of C$_n$H$_{(2n+2)}$O$_n$. Preferably these sugar alcohols are acyclic and unbranched. Examples of the C$_{(3-5)}$ sugar alcohol are glycerol, erythritol, threitol, arabitol, xylitol, ribitol, sorbitol and mannitol. For a toothpaste a mixture of glycerol and sorbitol is preferred, more preferably in glycerol amounts of 5 to 30%, still more preferably 15 to 25%, based on the toothpaste; and more preferably in sorbitol amounts of 5 to 30%, still more preferably 15 to 25%, based on the toothpaste. Still more preferably for toothpastes, the amounts are 17 to 27% of glycerol and 17 to 27% of sorbitol, particularly preferably 20 to 24% of glycerol and 20 to 24% of sorbitol. The one or more C$_{(3-6)}$ sugar alcohols are preferably dissolved in the liquid phase of the toothpaste.

The toothpastes of the invention may furthermore comprise an organic acid and/or salt thereof, either as part of a buffering system intended to achieve the above mentioned physiologically acceptable pH of the liquid phase, or as a complexing agent for dissolved tin species, if present. The organic acid, if present, is preferably a carboxylic acid. It is preferably dissolved in the liquid phase of the toothpaste. The term "dissolved" implies here that the acid be dissolved either as the free acid or as a pharmaceutically acceptable salt of its anionic conjugate base (whichever may be the case) in the liquid phase. Preferred subgroups of organic acids are edible di- or tricarboxylic acids with 4 to 6 carbon atoms including the carboxylate carbon atoms, such as succinic, tartaric, citric, malic, fumaric and adipic acids; or edible α-hydroxy C$_{(2-6)}$carboxylic acids such as glycolic, lactic, citric, tartaric or gluconic acids. If the organic acid is dissolved in the form of a pharmaceutically acceptable salt then the counter cation may be a metal cation, such as from an alkaline metal (such as sodium or potassium), from an earth alkaline metal (such as magnesium or calcium), or from zinc. When organic acid is present, then its content is preferably in the range of 0.01 to 10%, preferably 0.05 to 5%, based on the dentifrice, whereby the upper limit may be given by the solubility of its conjugate base salt in the liquid phase at physiologically acceptable pH. The total content of organic acids may be determined by acidifying a known aliquot of the oral care composition to about pH 0, extracting the free organic acids with an organic solvent such as ether, and analysing the extract by calibrated GC using the silyl esters derivates of the acids. More preferably the toothpastes of the invention contain 0.3 to 1.0% of gluconic acid or of a salt thereof (i.e. gluconate).

The toothpastes of the invention may preferably also comprise chloride ions, preferably as dissolved ions in the liquid phase of the toothpaste. A preferred range of the chloride content [Cl$^-$] in ppm, based on the toothpaste, is in the range 0.7[Sn]≥[Cl$^-$]≥0.5[Sn]. The chloride content may be determined by potentiometric titration (see example 12). The chloride may be added for example as sodium chloride, calcium chloride or stannous chloride, with the latter being preferred.

Further optional components in the dentifrices, in particular the toothpastes, may be for instance:

Flavourings and cooling flavours, such as coumarin, vanillin, ethereal oils (such as peppermint oil, spearmint oil, aniseed oil, menthol, anethol or citrus oil) or other essences (such as apple, eucalyptus or spearmint essence). These flavourings may be present in 0% to 0.5%, preferably 0.03% to 0.3%, based on the dentifrice.

Sweeteners, in particular artificial sweeteners such as saccharin, acesulfam, neotam, cyclamate or sucralose; natural high-intensity sweeteners such as thaumatin, stevioside or glycyrrhizin; or sugar alcohols different from the C$_{(3-5)}$ sugar alcohol, such as sorbitol, xylitol, maltitol or mannitol. These may be present in amounts of 0% to 0.2%, preferably 0.005% to 0.1%, based on the dentifrice.

Antibacterials and/or preservatives, such as chlorhexidine, triclosan, quaternary ammonium compounds (such as benzalkonium chloride) or parabens (such as methyl or propyl paraben). The amount of antimicrobial agent is typically from 0 to about 0.5%, preferably 0.05 to 0.1%, based on the dentifrice.

Emulsifiers or solubilisers, mainly in connection with abovementioned flavourings and/or antibacterials, which often are of low solubility in aqueous media. Examples of such emulsifiers are neutral surfactants (such as polyoxyethylene hydrogenated castor oil or fatty acids of sugars), anionic surfactants (such as sodium lauryl sulphate), cationic surfactants (such as the ammonium cations of formula (I)) or zwitterionic surfactants. These surfactants or solubilisers may be present in amounts of typically 0% to 2%, preferably 0.2% to 1.5%, based on the dentifrice.

Thixotropic agents, such as soluble grades of hydroxypropylmethylcellulose, hydroxyethylcellulose or mucins, in an amount effective to impart the dentifrice a thixotropic behaviour.

Stabilisers, such as polyvinylpyrrolidone.

The dentifrices or articles are intended for use against erosive tooth demineralisation. For this purpose they are suitably provided as a kit containing the composition and human-readable indications disclosing to the subject using the composition that the composition is for use, or efficacious, against erosive tooth demineralisation. These indications may be directly printed on the container comprising the dentifrice (such as a toothpaste tube), or they may be printed on a label wrapped or adhered onto the container. They may also be printed on a package, such as a cardboard box, enclosing the container. Finally they may be printed on a leaflet (a package insert), to be included into the kit.

The dentifrices, articles or kits of the invention may be used to prevent or treat erosive tooth demineralisation in a subject in need of such prevention or treatment. As "treatment" is preferably understood here the so-called "secondary prevention", which is a treatment on subjects exhibiting early or intermediate stages of erosive tooth demineralisation, in order to slow down a further progression of the demineralisation.

Patients in need of prevention are subjects having at least one of the following habits or conditions 1)-5):

1) They regularly consume acidic foods, in particular acidic beverages such as soft drinks;
2) they suffer from reflux disease or bulimia,
3) they clean their teeth to an extent to remove essentially all of the salivary pellicle on their tooth surfaces;
4) they have an anomaly in the chemical properties of their saliva, particularly such as below-normal levels of calcium and/or phosphate, or below-normal buffering capacity;
5) they exhibit insufficient saliva production (xerostomia patients).

Particularly patients in need of prevention are understood as subjects having 1) in combination with one of 3) to 5), or subjects having 2) in combination with one of 3) to 5). Patients in need of treatment, particularly in need of the abovementioned secondary prevention, are subjects having at least one of the above 1)-5), or having 1) in combination with one of 3) to 5), or having 2) in combination with one of 3) to 5); and furthermore showing the signs of early or intermediate stages of erosive tooth demineralisation.

As used throughout, ranges are used as shorthand for describing each and every value that is within the range including its boundary values. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention will now be further explained by the following non-limiting examples. In the examples "AmF" or "AmF 297" denotes the amine hydrofluoride OLAFLUR.

Example 1

In Situ Demineralisation Study on Enamel with Toothpastes Containing a Combination of the Invention The study products were three toothpastes according to the following table 3:

TABLE 1

| Composition | Entry 1 (Placebo) | Entry 2 | Entry 3 |
|---|---|---|---|
| Actives | | 3500 ppm Sn ex $SnCl_2$ 700 ppm F ex AmF 700 ppm F ex NaF | 3500 ppm Sn ex $SnCl_2$ 700 ppm F ex AmF 700 ppm F ex NaF 0.5% chitosan |
| AmF solution (1.4 wt. % fluoride) (%) | | 5.000 | 5.000 |
| $SnCl_2$ dihydrate (%) | | 0.675 | 0.675 |
| NaF (%) | | 0.155 | 0.155 |
| cocamidopropyl betain (%) | 3.500 | 3.500 | 3.500 |
| fragrance (%) | 1.350 | 1.350 | 1.350 |
| sodium saccharin (%) | 0.200 | 0.360 | 0.360 |
| glycerol (%) | 22.000 | 12.000 | 22.000 |
| sorbitol 70% (%) | 22.000 | 24.000 | 22.000 |
| sodium-D-gluconate (%) | 0.750 | 0.750 | 0.750 |
| hydroxyethyl cellulose (%) | 2.000 | 2.100 | 1.550 |
| hydrated silica (%) | 12.000 | 16.500 | 12.000 |
| Alumina (%) | 0.500 | 0.700 | 0.500 |
| methyl parabene (%) | 0.180 | | |
| propyl parabene (%) | 0.020 | | |
| titanium dioxide (%) | 1.000 | 1.000 | 1.000 |
| KOH 86% (%) | 0.032 | 0.300 | 0.140 |
| Chitosan (%) | | | 0.500 |
| HCl 10% (%) | | | 0.670 |
| demineralized water (%) | 34.468 | 31.610 | 27.850 |

The toothpaste indicated in bold is a toothpaste suitable for the invention, also forming per se part of the invention, the other ones are comparative toothpaste formulations.

The study included 10 male and female volunteers of 18 years and older; not having serious diseases, particularly those interfering with saliva flow rate; with healthy or sufficiently restored dentition and no removable dentures or orthodontic devices; not having clearly visible dental plaque; absence of signs of salivary hypofunction, not being allergic to previously used oral hygiene products, oral therapeutic agents or dental materials; not having medication interfering with saliva flow rate, and not being pregnant or giving breastfeeding.

One-hundred-eighty enamel specimens were prepared from freshly extracted, previously completely impacted human third molars. All donors lived in an area with ≤0.03 mg/L fluoride in the drinking water. The natural surfaces of enamel specimens were ground flat and polished under sufficient water flow (Exakt Abrasive Cutting System and Exakt Mikrogrinder, Exakt-Apparatebau, Norderstedt, Germany; P800 and P1200 silicon carbide abrasive paper, Leco, St. Joseph, USA). The preparation resulted in an experimental area of at least 3×3 mm². Specimens were stored in 100% humidity until use.

A total of 6 enamel specimens were recessed in the buccal aspects of mouth appliances, which were made from cold-cured acrylic and retained by braces. One half of the experimental area was covered with a light curing resin material (Technovit 7230 VLC, Kulzer-Exakt, Wehrheim, Germany) and served as the reference area for profilometry. After covering, specimens were scrutinized under a microscope (magnification 10×, SMZ-1, Zoom Stereomicroscope, Nikon GmbH, Düsseldorf, Germany) to ensure that there were no contaminations by the light curing resin on the experimental area. For disinfection, the specimens were stored in saturated aqueous thymol solution for at least 2 weeks. Before insertion into the mouth, the appliances with the specimens were immersed in 70% ethanol for 30 min.

The study used a crossover design with 4 experimental periods of 7 days (except weekends) each, meaning that each volunteer eventually came to test each of the four study products indicated in the above table, but in an order which was different for each volunteer. Before each of the four experimental period a 5-day wash-out period was included. During the four experimental periods, food and drinks with high fluoride content (tea, sea fish, mineral water, fluoridated table salt) were avoided best possible. Oral hygiene was performed habitually with the placebo toothpaste and the standardized toothbrush (elmex Sensitive toothbrush), without the mouth appliances in situ. No other fluoride containing products were used. The volunteers carried the appliances with the enamel samples in their mouths during day and night, except for meals. After meals or drinks, 15 min were allowed elapse before reinsertion of the appliances. For erosive demineralization, the mouth appliances were immersed extra-orally in 200 ml 5% (w/w) citric acid (pH 2.6; room temperature) for 6×2 min per day, starting at 8.30 a.m. and with intervals of 1.5 h between each demineralization. Immersion is performed under standardized agitation (30/min) at room temperature. After demineralization, the mouth appliances were rinsed with tap water for 1 min before reinsertion. After the first and the last demineralization per day, volunteers, wearing the mouth appliances, took a pea-size amount of toothpaste or gel on the powered toothbrush (Oral-B Professional Care 3000, Oral-B, Schwalbach am Taunus, Germany), brushed the occlusal surfaces of their own lower teeth for 15 seconds to produce a saliva/toothpaste suspension, swished around to the buccal area for 15 seconds and brushed each sample for 5 seconds. Volunteers were asked to place the head of the toothbrush adjacent to a sample on the mouth appliance, push until the pressure alert was activated (2.5 N) and then to move the toothbrush head on the sample without changing the pressure and to let the brush operate without further manual action and under visual control. After brushing, the toothpaste/saliva suspension was held in the mouth until a total time of 2 minutes was completed, followed by a rinse with tap water for 3 seconds. Afterwards, the mouth appliances were removed and rinsed under tap water for at least 1 minute until all visible remnants of toothpaste were removed. Samples on the left side of the appliance were brushed (samples on the right side for left-handers), samples on the other side were left unbrushed and are eroded only. The order of brushing was from anterior to posterior in the morning and from posterior to anterior in the evening. All application times were measured with stop watches. Every evening, the mouth appliances were immersed for 1 min in chlorhexidine digluconate solution to avoid plaque formation on specimens which were not brushed. The mouth appliances (except the samples) were brushed without toothpaste. The demineralization solution is renewed at the beginning of each day. After each experimental period, the test products were collected and weighted. The brushing heads were renewed for each treatment period. After each of the four experimental periods the 6 erosion tested enamel specimens were carefully removed from each the mouth appliances and fixed with acrylic resin on glass slides.

Before analysis, the acrylic cover was carefully removed from all enamel specimens, and the surfaces were checked in view of acrylic remnants or damage. Measurement was performed with an optical profilometry device (MicroProf, Fries Research&Technology GmbH, Bergisch-Gladbach, Germany). On each sample, three profilometric traces were made at intervals of 0.2 mm, each 2 mm in length (200 pixel, 32 hertz, sensor HO). Traces were interpreted with special software (Mark III, Fries Research&Technology GmbH Bergisch-Gladbach, Germany). Two regression lines were constructed on each trace: one on the reference area and one on the experimental area, both 0.3 mm in length. The midpoints of both regression lines were calculated by software. The vertical distance between the midpoints was defined as tissue loss (µm).

The primary outcome measure was the profilometrically measured tissue loss at the end of the experimental period of 7 days, expressed in micrometres. The observation unit was the volunteer; therefore the mean tissue loss of the three enamel specimens was used. All statistical procedures were performed with SPSS 18.0 for Windows (SPSS, Chicago, Ill., USA). The Kolmogorov-Smirnov test was used for checking deviations from the Gaussian distribution, homogeneity of variance will be checked with the Levene-test. An analysis of variance (ANOVA) with Tukeys post-hoc test was performed to compare the groups. The level of significance for all analyses was set at 0.05.

The obtained results (mean and standard deviation SD from the 10 volunteers) are as in the following table 2.

TABLE 2

| Entry of table 1 | enamel loss [micrometres] slurry without brushing | | enamel loss $d_x$ [micrometres] slurry with brushing | |
|---|---|---|---|---|
| | Mean | SD | mean of $d_x$ | SD of $d_x$ |
| 1 | 11.20 | 4.59 | 17.67 | 4.71 |
| 2 | 3.62 | 1.88 | 12.83 | 6.44 |
| 3 | 2.75 | 2.79 | 9.61 | 5.62 |

Table 2 firstly shows that more enamel is lost in all cases with brushing than without brushing. This is because partly demineralized enamel, as studied in this example, is generally more prone to be removed by brushing than healthy enamel. It firstly can be seen that the inventive toothpaste (entry 3) outperforms the placebo toothpaste having similar excipients but being devoid of both fluoride and chitosan (entry 1), and outperforms a comparative toothpaste having similar fluoride and dissolved tin content but being devoid of chitosan (entry 2). The toothpastes as described herein can thus be used, due to their favourably high PCR values, on demineralized teeth to remove plaque and biofilms from teeth to an acceptable level without simultaneously erasing the demineralized dentin or enamel to an unacceptably high extent.

Examples 2-6

Toothpaste Formulations Suitable for the Uses and Processes for the Invention

TABLE 3

| Example No. | 2 | 3 | 4 | 5 | 6 |
|---|---|---|---|---|---|
| actives | 3500 ppm $Sn^{2+}$ ex $SnCl_2$ 700 ppm F- ex AmF 700 ppm F- ex NaF 0.5% Chitosan | 3500 ppm $Sn^{2+}$ ex $SnCl_2$ 700 ppm F- ex AmF 700 ppm F- ex NaF 0.5% Chitosan | 3500 ppm $Sn^{2+}$ ex $SnCl_2$ 700 ppm F- ex NaF 700 ppm F- ex AmF 0.5% Chitosan | 3500 ppm $Sn^{2+}$ ex $SnCl_2$ 700 ppm F- ex AmF 700 ppm F- ex NaF 0.5% Chitosan | 3500 ppm $Sn^{2+}$ ex $SnCl_2$ 700 ppm F- ex AmF 700 ppm F- ex NaF 0.5% Chitosan |
| glycerol (%) | 22.000 | 10.000 | 22.000 | 10.000 | 12.000 |
| sorbitol 70% (%) | 22.000 | 21.000 | 22.000 | 21.000 | 24.000 |
| sodium gluconate (%) | 0.750 | | 0.750 | 1.000 | 0.750 |
| hydroxyethyl-cellulose (%) | 1.550 | 1.650 | 1.550 | 1.700 | 1.600 |
| hydrated silica (%) | 12.000 | 12.000 | 12.000 | 16.000 | 16.500 |
| alumina (%) | 0.500 | 0.500 | 0.500 | 0.700 | 0.700 |
| cocamidopropyl betaine (%) | 3.500 | 3.500 | 3.500 | 3.500 | 3.500 |
| fragrance (%) | 1.470 | 1.400 | 1.350 | 1.350 | 1.350 |
| sodium saccharin (%) | 0.200 | 0.200 | 0.360 | 0.360 | 0.360 |
| titanium dioxide (%) | 1.000 | 1.000 | 1.000 | 1.000 | 1.000 |
| demineralized water (%) | 28.400 | 42.100 | 27.850 | 35.960 | 31.060 |

The compositions are adjusted to a pH in the liquid phase of about 4.5 using small amounts of 37% HCl and/or 25% NaOH.

Example 7

Determination of the Total Content of Dissolved Tin [Sn] by X-ray Fluorescence in an Oral Care Composition As the x-ray fluorescence spectrometer a Thermo Noran QuanX is used. Two solutions are measured:

Solution 1: 5 g of the oral care composition is directly filled into a XRF-cup. The XRF-cup is then closed with a polyethylene foil with the appropriate closing ring and is followingly inserted into the autosampler of the instrument.

Solution 2 is as solution 1, but with a known amount of furthermore added stannous salt [ΔSn] in the range of 80% to 120% of the expected ppm value of [Sn] of the sample solution.

Solutions 1 and 2 are each irradiated for 600 seconds with x-ray at 50 kV excitation, using a copper filter, $K_\alpha$-line at 25.193 keV. The integrated area under the fluorescence intensity peak of solution 1 is taken as $A_1$ and the integrated area under the fluorescence intensity peak of solution 2 is taken as $A_2$.

The dissolved tin content in ppm based on the composition, [Sn], is obtained as $$[Sn] = [\Delta Sn]\frac{A_2}{A_2 - A_1}$$

Example 8

Measurement of Dissolved Tin at Formal Oxidation State +II in an Oral Care Composition A combined platinum electrode type 6.1204.310 of Metrohm, Switzerland, and a potentiometer Titrando 809 of Metrohm, Switzerland, are used. The calibration of the electrode is done according to the manual.

10.0000 g of the oral care composition are exactly weighed (±0.1 mg) in a 100 ml container and 40 ml water, 5 ml 32% HCl and a known aliquot v (in ml) of standard 0.05 M $KI_3$ solution is added, such that iodine is added in excess of the tin in formal oxidation state +II contained in the sample (a typical value for v is 5 ml).

The electrode is immersed into the sample solution and the remaining iodine not already reduced to $I^-$ by the tin in formal oxidation state +II is titrated back with standard 0.1 M $Na_2S_2O_3$ solution to the endpoint of the titration. The used amount of $Na_2S_2O_3$ solution in ml is taken as $v_1$.

The tin in formal oxidation state +II contained in the sample in ppm based on the oral composition, $[Sn^{+II}]$, is obtained as $$[Sn^{+II}]=593.45(v-v_1)$$

Example 9

Potentiometric Fluoride Determination in an Oral Care Composition

A fluoride-selective electrode type 6.0502.150 of Metrohm, Switzerland, a pH/Ion-meter 692, Metrohm, Switzerland and an Ag/AgCl reference electrode type 6.0750.100, Metrohm, Switzerland are used.

A total ionic strength adjusted buffer (TISAB) is required and made as follows: A solution of 160 mg NaOH in 2 litres of water is prepared (solution 1); 25 g 1,2-diaminocyclohexane-N,N,N',N'-tetraacetic acid, 290 g NaCl and 285 ml glacial acetic acid are dissolved in 2 litres of water (solution 2); then solutions 1 and 2 are mixed and filled up to 5 litres with water.

The calibration of the fluoride-selective electrode is performed according to the manual of the pH/Ion-meter.

1.0000 g±0.1 mg of the oral care composition are exactly weighed in a 50 ml plastic container and filled up with water to a weight of 20.0000 g±0.1 mg, and 20 ml of above mentioned TISAB buffer are added. The fluoride-selective electrode and the reference electrode are immersed into the sample and the potential is read off after 5 minutes, according to the manual of the pH/Ion-meter. The fluoride concentration in ppm is calculated by multiplying the measured response-value by 40 (the total dilution factor from the oral care composition to the measured sample), and dividing by the weight of the oral care composition sample in g.

Example 10

Determination of Ammonium Cations of Formula R—NH$^+$R$_a$—[(CH$_2$)$_u$—NH$^+$R$_b$]$_v$—R$_c$, with R$_a$, R$_c$=Hydrogen and v=0, or with R$_b$, R$_c$=Hydrogen and v=1, in an Oral Care Composition The determination is done using densitometric quantification on reverse phase HPTLC plates after staining with ninhydrine.

Procedure:

Ninhydrine solution: Dissolve 2 g of ninhydrine purum in 1000 ml of ethanol p.a. The solution has to be stored in a glass bottle at 4° C. (maximal storage time: 1 month).

A reference solution of the ammonium cation to be determined is prepared by dissolving an exactly known amount of the corresponding pure amine hydrofluoride in methanol p.a., to make a solution containing an exactly known content of the amine fluoride in the range of about 3000 ppm, based on the solution. This reference solution is designated in the following as R.

Sample solution: Accurately weigh (to within 0.1 mg) an amount M of approximately 1 g of the oral care composition in a 25 ml measuring flask and make up to volume with methanol p.a. Expose to ultrasonic radiation for about 20 minutes. This solution is designated as S.

The HPTLC plate is Silicagel 60 without fluorescence indicator, 10×20 cm (Merck no. 5626).

The reference solution and the sample solution are applied onto the HPTLC plate using an applicator Linomat IV (Camag, Switzerland) according to the following track scheme:

| Track No. | Solution | Amount applied (µl) |
|---|---|---|
| 1 | R | 2 |
| 2 | S | 10 |
| 3 | R | 4 |
| 4 | S | 10 |
| 5 | R | 6 |
| 6 | S | 10 |
| 7 | R | 8 |
| 8 | S | 10 |
| 9 | R | 10 |
| 10 | S | 10 |
| 11 | R | 2 |
| 12 | S | 10 |
| 13 | R | 4 |
| 14 | S | 10 |
| 15 | R | 6 |
| 16 | S | 10 |
| 17 | R | 8 |
| 18 | S | 10 |
| 19 | R | 10 |
| 20 | S | 10 |

Each track has an initial width on the plate of 4 mm; the initial distance between two tracks is 5 mm and the initial distance from one outermost track to the adjacent edge of the plate is 11 mm.

The plate is developed with ethanol: 25% aqueous ammonia 9:1 (v/v) as the eluent to a migration distance of about 6 cm (under these conditions e.g. the ammonium cation of formula (I) with R$_a$, R$_c$=hydrogen and R=9-octadecen-1-yl migrates to an R$_f$ value of about 0.6). The plate is then immersed in the ninhydrine solution for 10 min and dried for 10 min at 100° C.

Calculation:

The areas of all developed spots are evaluated densitometrically with light of wavelength 480 nm using a TLC scanner 3 (CAMAG, Switzerland).

The areas obtained from tracks 1, 3, 5, 7 and 9 are used to obtain a first parabolically approximated calibration curve of area vs. amount of amine fluoride in µg. A second such calibration curve is obtained from tracks 11, 13, 15, 17 and 19.

The average area from sample tracks 2, 6, 10, 14 and 18 is converted to an amount [am1] amine fluoride in µg using the first calibration curve. The average area from sample tracks 4, 8, 12, 16 and 20 is similarly converted to an amount [am2] amine fluoride in µg using the second calibration curve.

The content of ammonium cations of formula (I) I ppm, based on the oral care composition, [AM], is then obtained as $$[AM] = \frac{1250([am1] + [am2])}{M} \times \frac{(MW - 19(v+1))}{MW}$$

wherein M, [am1] and [am2] are as defined above, MW is the molecular weight of the pure amine fluoride used to prepare solution R, and v is as defined for formula (I).

Example 11

Determination of Ammonium Cations of Formula R—NH$^+$R$_a$—[(CH$_2$)$_u$—NH$^+$R$_b$]$_v$—R$_c$, Derived from Amine Fluoride in an Oral Care Composition The procedure of this example is applicable to all other ammonium cations of formula (I) not falling under the definitions given in the heading of example 6. This determination is done on reverse phase HPTLC plates after staining with Berlin Blue.

Berlin Blue solution: Dissolve 4 g of potassium hexacyanoferrate(III) p.a. in 150 ml distilled water and add 350 ml of acetone p.a. Dissolve separately 7.5 g iron(III)chloride hexahydrate p.a. in 500 ml ethanol p.a. Mix immediately prior to use 40 ml of each of the two solutions and 80 ml of ethanol p.a.

A reference solution of the ammonium cation to be determined is prepared by dissolving an exactly known amount of the corresponding pure amine hydrofluoride in methanol p.a., to make a solution containing an exactly known content of the amine fluoride in the range of about 500 ppm, based on the solution. This reference solution is designated as R.

Sample solution: Accurately weigh (to within 0.1 mg) an amount M of approximately 1 g of the oral care composition in a 100 ml measuring flask and make up to volume with methanol p.a. Expose to ultrasonic radiation for about 15 minutes. This solution is designated as S.

The HPTLC plate is Silicagel 60 without fluorescence indicator, 10×20 cm (Merck no. 5626).

The reference solution and the sample solution are applied onto the HPTLC plate using an applicator Linomat IV (Camag, Switzerland) according to the following track scheme:

| Track No. | Solution | Amount applied (µl) |
|---|---|---|
| 1 | R | 1 |
| 2 | S | 3 |
| 3 | R | 2 |
| 4 | S | 3 |
| 5 | R | 3 |
| 6 | S | 3 |
| 7 | R | 4 |
| 8 | S | 3 |
| 9 | R | 5 |
| 10 | S | 3 |
| 11 | R | 1 |
| 12 | S | 3 |
| 13 | R | 2 |
| 14 | S | 3 |
| 15 | R | 3 |
| 16 | S | 3 |
| 17 | R | 4 |
| 18 | S | 3 |
| 19 | R | 5 |
| 20 | S | 3 |

Each track has an initial width on the plate of 4 mm; the initial distance between two tracks is 5 mm and the initial distance from one outermost track to the adjacent edge of the plate is 11 mm.

The plate is developed with n-pentanol:ethanol:diethyl ether:25% aqueous ammonia 3:3:3:1 (v/v/v/v) as the eluent to a migration distance of about 6 cm (under these conditions e.g. the ammonium cation of formula (I) with $R_a$, $R_b$, $R_c$=2-hydroxyethyl, R=9-octadecen-1-yl, v=1 and u=3 migrates to an $R_f$ value of about 0.8). The plate is then immersed in the Berlin Blue solution for 10 min and dried for 10 min at 100° C.

Calculation:

The areas of all developed spots are evaluated densitometrically with light of wavelength 592 nm using a TLC scanner 3 (CAMAG, Switzerland).

The areas obtained from tracks 1, 3, 5, 7 and 9 are used to obtain a first parabolically approximated calibration curve of area vs. amount of amine fluoride inn. A second such calibration curve is obtained from tracks 11, 13, 15, 17 and 19.

The average area from sample tracks 2, 6, 10, 14 and 18 is converted to an amount [am1] amine fluoride in µg using the first calibration curve. The average area from sample tracks 4, 8, 12, 16 and 20 is similarly converted to an amount [am2] amine fluoride in µg using the second calibration curve.

The content of ammonium cations of formula (I) I ppm, based on the oral care composition, [AM], is then obtained as $$[AM] = \frac{100000([am1] + [am2])}{6M} \times \frac{(MW - 19(v+1))}{MW}$$

wherein M, [am 1] and [am2] are as defined above, MW is the molecular weight of the pure amine fluoride used to prepare solution R, and v is as defined for formula (I).

Example 12

Potentiometric Chloride Determination in an Oral Care Composition

A combined silver/silver chloride electrode type 6.0350.100 of Metrohm, Switzerland, and a potentiometer Titrando 809 of Metrohm, Switzerland, are used. The calibration of the electrode is done according to the manual.

1000±0.1 mg of the oral care composition are exactly weighed in a 100 ml plastic container and 50 ml water and 2 ml 65% nitric acid are added.

The electrode is immersed into the sample and the sample is titrated with standard 0.01 M silver nitrate solution to the endpoint of the titration. The used volume of silver nitrate solution in ml is taken as v.

The chloride contained in the sample in ppm based on the composition, [Cl⁻], is obtained as $$[Cl^-] = 354.5v$$

Example 13

Determination of the Degree of Deacetylation (DDA) of a Chitosan Sample

The DDA is determined on the fully protonated chitosan sample by direct titration using NaOH as a titrant. The amount of NaOH used between the pH range of 3.75 and 8.00 gives a way to calculate the degree of deacetylation in the chitosan sample. The chitosan is used in powder form of at the most 20 mesh particle size, if necessary the chitosan is ground beforehand to obtain such particle size. 100.0 mg of such chitosan powder, corrected for dry matter content, are accurately weighted, dissolved in 25 ml of 0.06 M HCl and stirred for 1 hour at room temperature until full dissolution. The solution is then diluted to 50 ml with 25 ml deionized water. The pH of the solution is now about 1.9. This solution is titrated from a buret with standardized 0.1000 N NaOH solution under stirring using a calibrated glass pH electrode, until the solution reaches a pH of 3.75. The buret volume reading at this point (in ml) is taken as $V_1$. Titration with standardized 0.1000 N NaOH under stirring is continued until the solution has a pH of 8.00 remaining stable for 10 seconds. The buret volume reading at this point (in ml) is taken as $V_2$. The DDA is then calculated according to the formula $$DDA = \frac{16116 * (V_2 - V_1) * N}{(W_1)}$$

wherein $V_1$ is the buret volume reading at pH=3.75, $V_2$ is the buret volume reading at pH=8.00 stable for 10 seconds, N is the concentration of NaOH in moles/liter, i.e. 0.1000 moles/liter, and $W_1$ is the weighted amount of moisture corrected chitosan in milligrams, i.e. 100.0 mg.

Example 14

Determination of the Pellicle Cleaning Ratio (PCR) in a Toothpaste

The determination is done by photometric measurement of in vitro stain on lightly etched enamel specimens before and after brushing with of the toothpaste to be tested.

Bovine, permanent, central incisors are cut to obtain labial enamel specimens approximately 10 mm×10 mm. The enamel specimens are embedded in an autopolymerizing methacrylate resin so that only the enamel surfaces are exposed. The enamel surfaces are then smoothed and polished on a lapidary wheel and lightly etched to expedite stain accumulation and adherence. They are placed on a rotating rod (in 37° C. incubator) which alternately exposes them to air and to a solution consisting of trypticase soy broth, tea, coffee, mucin, $FeCl_3$, and *Sarcina lutea*. The staining broth is changed and specimens rinsed daily until a uniform stain has accumulated. After approximately seven days, a darkly stained pellicle film is normally apparent on the enamel surfaces. Specimens are rinsed, allowed to air dry, and refrigerated until use. All products are tested using specimens prepared at the same time.

The amount of in vitro stain is graded photometrically (Minolta CR221b, ChromaMeter) using only the L value of the LAB scale. The area of the specimens scored is a ¼-inch diameter circle in the center of the 10 mm×10 mm enamel. Specimens with scores between 23-42 (23 being more darkly stained) are used. On the basis of these scores, the specimens are divided into groups of 16 specimens each, with each group having the same average baseline score.

The specimens are mounted on a mechanical V-8 crossbrushing machine equipped with soft nylon-filament (Oral-B 40) toothbrushes. Tension on the enamel surface is adjusted to 150 g. The toothpaste is tested as a slurry prepared by mixing 25 g of the toothpaste with 40 ml of deionized water. The reference material is the ADA abrasion standard (10 g calcium pyrophosphate/50 ml of a 0.5% CMC solution). The specimens are brushed for 800 strokes (4½ minutes).

To minimize mechanical variables, one specimen per group is brushed on each of the eight brushing heads. Different test products are used on each run, with one tube of slurry made up for each product. Fresh slurry is made after being used to brush four specimens. Following brushing, specimens are rinsed, blotted dry, and scored again for stain, as previously described.

The difference between the pre- and post-brushing stain scores is determined and the mean and standard error calculated for the reference group in each study. The cleaning ratio for the reference material group is assigned a value of 100. The mean stain decrement for each reference group is then divided into 100 to obtain a constant value to multiple times each individual test decrement within the study. The individual cleaning ratio for each specimen is then calculated (increment X constant). The mean and SEM for each group (N=16) is then calculated using the individual cleaning ratios. The larger the value of the cleaning ratio, the greater the amount of stained pellicle removed by the toothpaste tested.

Statistical analyses are performed with a one-way analysis of variance model using Sigma Stat Software (2.0). If significant differences are indicated, the individual means will be analyzed by the Student-Newman-Keuls (SNK) test. (If running two groups or less insert T-Test instead of SNK).

What is claimed is:

1. A dentifrice comprising 0.4 to 0.6% chitosan or pharmaceutically acceptable acid addition salt thereof, 1300 to 1500 ppm fluoride ions and an abrasive, for use against erosive tooth demineralization, wherein the dentifrice is a toothpaste comprising a liquid phase and comprising 3500 ppm tin dissolved in the liquid phase;
   wherein the fluoride ions are a combination of amine fluoride and sodium fluoride,
   wherein the chitosan or pharmaceutically acceptable acid addition salt thereof and the fluoride ions are dissolved in the liquid phase; and
   the chitosan comprises unmodified chitosan.

2. The dentifrice of claim 1, wherein the toothpaste comprises one or more abrasives in a total amount such as to impart the toothpaste a pellicle cleaning ration (PCR) value of at least 50.

3. The dentifrice of claim 1 wherein the dentifrice comprises 17 to 27% of glycerol, 17 to 27% of sorbitol, all % being based on the toothpaste; and one or more abrasives in a total amount such as to impart the toothpaste a pellicle cleaning ratio (PCR) value of at least 50.

4. The dentifrice of claim 3 further comprising 0.2 to 0.5% of chloride, 25 to 35% of water, 1 to 2% of hydroxyethylcellulose and 3 to 4% of cocamidopropyl betaine, all % being based on the toothpaste.

5. The dentifrice of claim 3, further comprising 20 to 24% of glycerol, 20 to 24% of sorbitol, 0.3 to 0.4% of chloride, 0.4 to 0.6% of gluconate and 27 to 32% of water, all % being based on the toothpaste.

6. A method for the prevention of erosive tooth demineralization or for the treatment of teeth affected by erosive tooth demineralization in a subject in need of such prevention or treatment, comprising bringing the subject's teeth in contact with the dentifrice of claim 1.

7. The method of claim 6, wherein the toothpaste comprises one or more abrasives in a total amount such as to impart the toothpaste a pellicle cleaning ratio (PCR) value of at least 50; and wherein the subject's teeth are affected by erosive tooth demineralization.

8. The dentifrice of claim 1, wherein the dentifrice comprises 5 to 30% of a mixture of glycerol and sorbitol and 0.3 to 1% of gluconate, all % being based on the toothpaste; and one or more abrasives in a total amount such as to impart the toothpaste a pellicle cleaning ratio (PCR) value of at least 50.

9. The dentifrice of claim 1 wherein the dentifrice comprises 5 to 30% of glycerol, 5 to 30% of sorbitol and 0.3 to 1% of gluconate, all % being based on the toothpaste;
   and one or more abrasives in a total amount such as to impart the toothpaste a pellicle cleaning ratio (PCR) value of at least 50.

* * * * *

UNITED STATES PATENT AND TRADEMARK OFFICE
CERTIFICATE OF CORRECTION

PATENT NO. : 10,653,605 B2
APPLICATION NO. : 13/985570
DATED : May 19, 2020
INVENTOR(S) : Dally Moya Argilagos et al.

Page 1 of 1

It is certified that error appears in the above-identified patent and that said Letters Patent is hereby corrected as shown below:

In the Specification

In Column 17, Line 62, delete "inn." and insert -- µg. --, therefor.

In the Claims

In Column 20, Line 25, in Claim 2, delete "ration" and insert -- ratio --, therefor.

Signed and Sealed this
Twenty-fifth Day of August, 2020

Andrei Iancu
*Director of the United States Patent and Trademark Office*